United States Patent [19]
Blakeley

[11] Patent Number: 5,257,930
[45] Date of Patent: Nov. 2, 1993

[54] SPEECH THERAPY APPLIANCE

[76] Inventor: Robert W. Blakeley, 248 NW. Seblar Ct., Portland, Oreg. 97210

[21] Appl. No.: 795,755

[22] Filed: Nov. 21, 1991

[51] Int. Cl.⁵ .................. A61C 3/00; A61C 13/02; G09B 19/04; A61F 2/20
[52] U.S. Cl. ............................ 433/6; 623/9; 433/168.1; 434/185
[58] Field of Search ............ 433/6, 10, 11, 168.1, 433/172, 178, 190; 623/9; 434/185

[56] References Cited

U.S. PATENT DOCUMENTS

| | | | |
|---|---|---|---|
| 2,748,480 | 6/1956 | Weissman | 433/178 |
| 3,259,129 | 7/1966 | Tepper | 433/6 X |
| 3,277,892 | 10/1966 | Tepper | 433/6 X |
| 3,462,837 | 8/1969 | Andrews et al. | 433/190 |
| 3,556,093 | 1/1971 | Quick | 433/6 X |
| 4,112,596 | 9/1978 | Fletcher et al. | 35/35 |
| 4,299,568 | 11/1981 | Crowley | 433/6 |
| 4,334,542 | 6/1982 | Takinishi et al. | 128/642 |
| 4,413,978 | 11/1983 | Kurz | 433/6 |
| 4,519,386 | 5/1985 | Sullivan | 128/136 |
| 4,706,292 | 11/1987 | Torgeson | 381/70 |
| 4,755,139 | 7/1988 | Abbatte et al. | 433/6 |
| 4,773,853 | 9/1988 | Kussick | 433/6 |
| 4,995,811 | 2/1991 | Cecconi | 433/190 |
| 5,096,416 | 3/1992 | Hulsink | 433/6 |

OTHER PUBLICATIONS

Neil et al., "The General Dentist's Role in Swallowing and Speech Aid Applicances," *Texas Dental Journal* 19-22 (Feb. 1990).

Siegel et al., "Magnitude Estimation of Oral Cavity Distances," *J. of Speech and Hearing Research* 26:574-578 (Dec. 1983).

*Hearsay* vol. 14, No. 3 (May-Jun. 1976).

*Primary Examiner*—David Isabella
*Assistant Examiner*—Elizabeth M. Burke
*Attorney, Agent, or Firm*—Klarquist, Sparkman, Campbell, Leigh & Whinston

[57] ABSTRACT

A method and device that facilitates production of r sounds in humans who have difficulty pronouncing them. An appliance is placed adjacent the posterior edge of the hard palate that lowers the effective roof of the palatal vault. The appliance preferably extends between the last erupted posterior maxillary teeth on each side of the dental arch, and lowers the palatal vault of the occlusal plane of the teeth between which the appliance extends. The position of the appliance in a subject's mouth can be manipulated by a handle, or the appliance can be fixed in a subject's mouth using dental clasps.

27 Claims, 3 Drawing Sheets

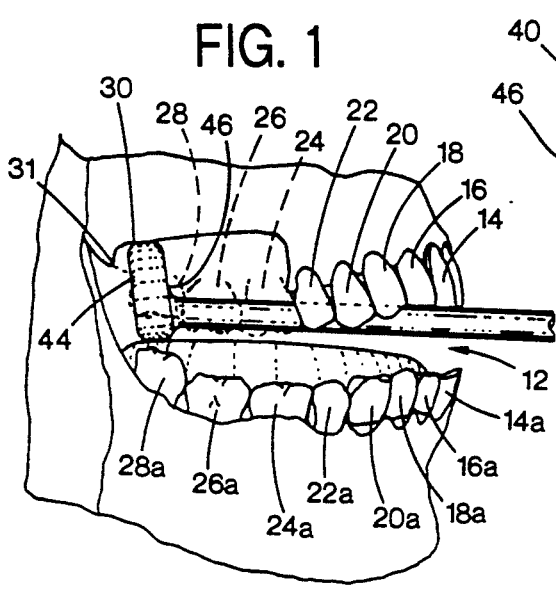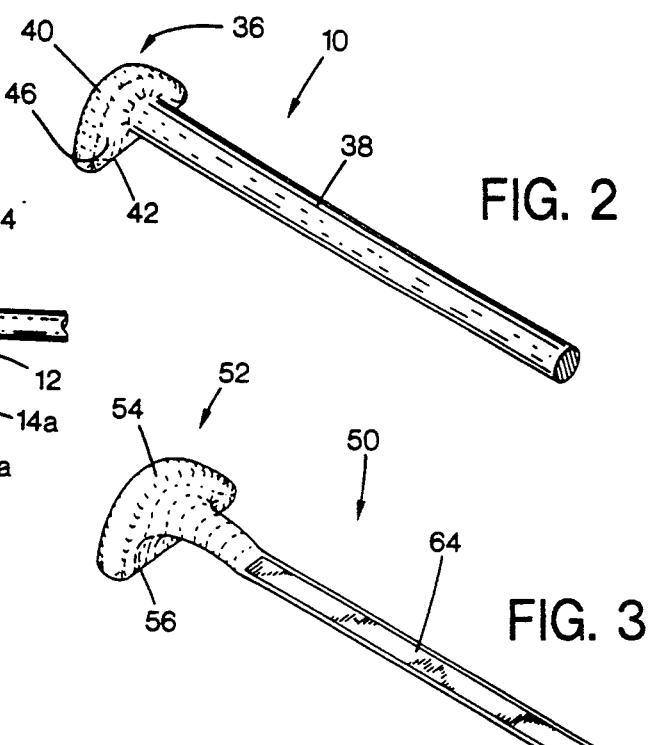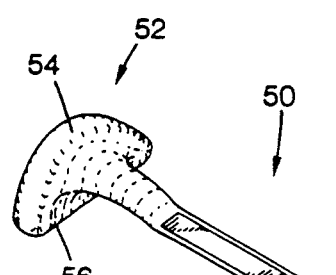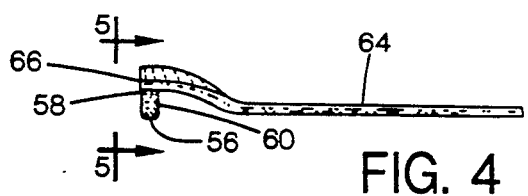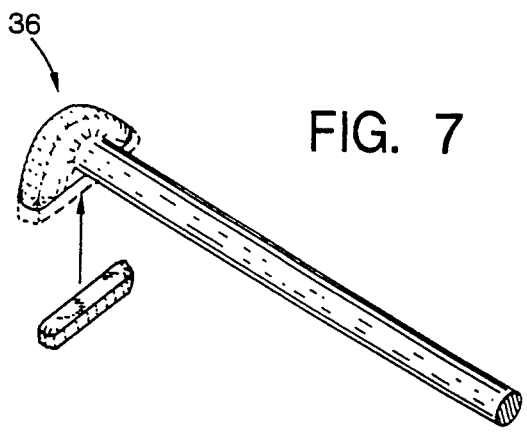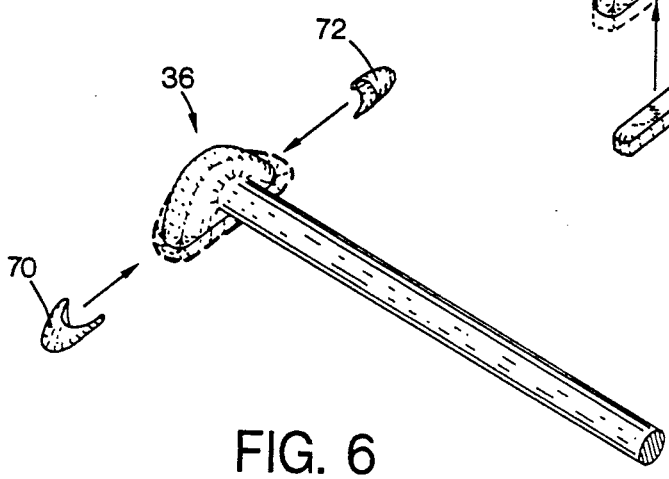

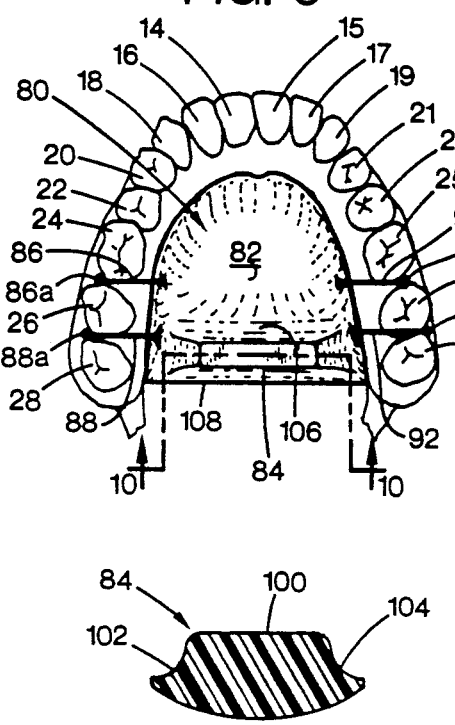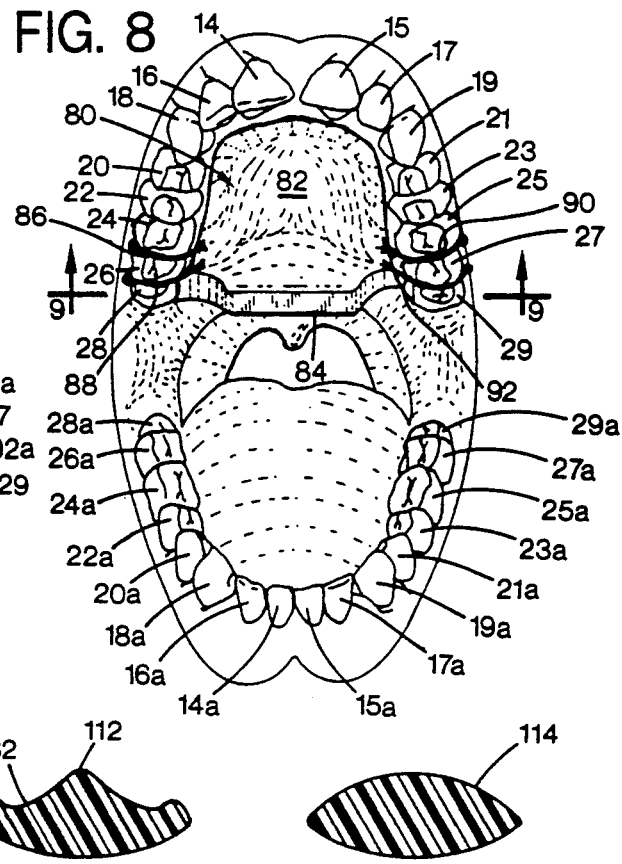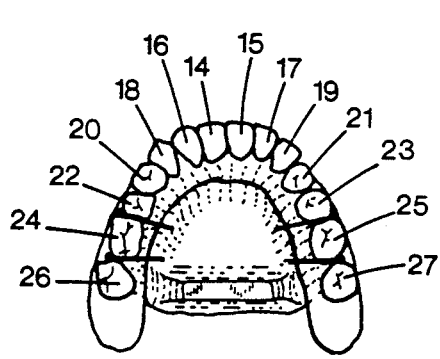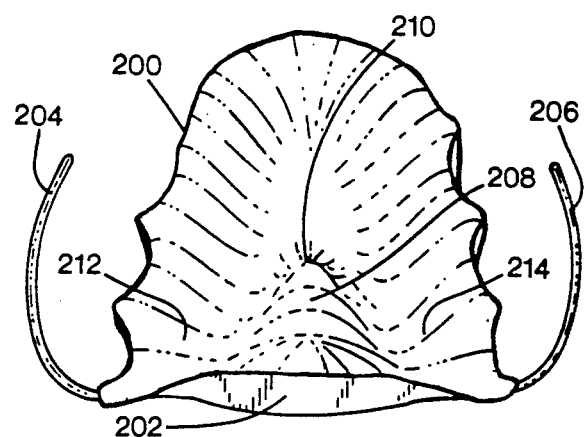

SPEECH THERAPY APPLIANCE

FIELD OF THE INVENTION

This invention concerns a prosthetic device for helping overcome speech problems, particularly difficulties pronouncing r sounds.

GENERAL DISCUSSION OF THE BACKGROUND

The phoneme /r/ is one of the five most used English consonants. Its frequency of occurrence in spoken English consonants is approximately 9%. There are several sound variations, called allophones, within the phoneme /r/. The phoneme is considered a consonant when it initiates a syllable (as in the word "red") or when it occurs in a consonant blend (e.g. "dr" as in dress). It is considered vocalic or vowelized when it occurs within a syllable (e.g. bird) or in a postvocalic position (as in water). The symbol for the vowel r is ɝ.

Difficulty pronouncing r sounds is one of the residual errors most often found in school age children. The persistence of this error may be related to the difficulty of correcting misarticulation of this phoneme. The tongue shape and position when articulating r are not easily visible, which makes it a difficult sound to teach and learn by imitation. Traditional speech therapy, however, has relied almost exclusively on instructional, auditory techniques to teach the phoneme /r/ and other troublesome speech sounds. For example, a clinician will teach a subject auditory discrimination by clarifying the differences between sounds, then may give verbal instruction for reproducing the sound by showing the subject how his mouth and tongue can be used to produce it. The patient will in turn learn to listen carefully to his sound production, and learn to produce the desired sound by imitating the auditory sample, and sometimes the mouth movements, prescribed by the therapist. Teaching r sounds has proven particularly difficult using these methods, particularly after habituation of the error has occurred.

In spite of its drawbacks, most contemporary speech articulation intervention is instructional, and does not rely on instrumentation or appliances to assist in desired sound production. The few speech therapy instruments that have been developed have been so complex that their use has been restricted to laboratories. Chaung and Wang, for example, used a reflected light method to study continuous tongue movements that produce Chinese sounds J. of Speech and Hearing Research 21:482–496 (1978) Barlow and Abbs used force transducers for evaluating labial, lingual and mandibular motor impairments. J. of Speech and Hearing Research 26:616–621 (1983). Siegel and Hanlon studied tactile sensitivity in the mouths of subjects by placing in subjects' mouths a variety of different artificial palates having varying shapes. J. of Speech and Hearing Research 26:574–578 (1983). An orometric system of electro-palatography was used by Fletcher and Hasegawa to set tongue, lip and jaw movements in a deaf child. J. of Speech and Hearing Disorders 48:148–184 (1983). Other methods of electro-palatography have been disclosed by Fletcher, J. of Speech and Hearing Disorders 50:254–261 (1985), Michi et al., J. of Speech and Hearing Disorders 51:226–238 (1986) and in U.S. Pat. Nos. 4,112,596 and 4,334,542.

The complexity of these devices has all limited their therapeutic clinical use. Moreover, these devices have primarily been diagnostic, without providing much therapeutic benefit that directly addresses or treats misarticulation disorders.

It is accordingly an object of the present invention to provide an appliance that facilitates the production of r sounds, particularly the vocalic ɝ, in human subjects who have difficulty articulating those sounds.

It is another object of the invention to provide such an improved device that is relatively simple and easy to use.

Yet another object is to provide such an improved device that can be simply and inexpensively manufactured.

These and other objects of the invention will be understood more clearly by reference to the following detailed description and drawings.

SUMMARY OF THE INVENTION

These objects are achieved with a method and device that facilitates production of r sounds, especially ɝ, in a person who has difficulty pronouncing such sounds. In the method of the present invention, an appliance is placed in the subject's mouth that lowers the effective roof of the palatal vault, preferably to the occlusal plane. In preferred embodiments, a block-like appliance is placed adjacent the posterior edge of the hard palate such that it extends across the hard palate between the last opposing erupted posterior maxillary teeth. In other embodiments, the appliance extends forward further, but preferably tapers progressively upward as it extends anteriorly. The preferred superior-inferior dimension between the last erupted teeth is sufficient for the device to extend from the hard palate to the occlusal plane. The anterior-posterior dimension preferably does not exceed the lingual distance of the last erupted pair of molars on opposite sides of the maxillary dental arch.

In one embodiment, the appliance is secured in a subject's mouth by a clasp that clips to the subject's teeth. Alternatively, the appliance can be positioned in the subject's mouth by attaching the appliance to an insertion rod, that is then used to position the appliance adjacent the posterior edge of the hard palate such that the appliance extends between the last erupted maxillary molars. The rod can have a curved distal portion that conforms to the shape of the roof of the mouth, and thereby minimizes interference with tongue movements. The appliance can be modified to change its size or shape by adding or deleting moldable material to the appliance.

BRIEF DESCRIPTION OF THE DRAWINGS

FIG. 1 is a schematic side view showing one embodiment of the device positioned in a subject's palatal vault.

FIG. 2 is a perspective view of the appliance shown in FIG. 1.

FIG. 3 is a top perspective view of an alternative embodiment of the appliance.

FIG. 4 is a side elevational view of the appliance shown in FIG. 3.

FIG. 5 is an end elevational view taken along view lines 5—5 of FIG. 4.

FIG. 6 is a view, similar to FIG. 2, showing how the size and shape of the appliance can be modified by placing moldable material on the lateral and inferior portions of the device.

FIG. 7 is a view, similar to FIG. 6, showing augmentation of the inferior surface of the device.

FIG. 8 is a schematic view showing placement of another embodiment of the device in the oral cavity of an adult.

FIG. 9 is a view taken along lines 9—9 in FIG. 8 showing the appliance in place on the upper dental arch.

FIG. 10 is a view taken along lines 10—10 in FIG. 9, showing the cross-sectional configuration of the portion of the appliance that projects down from the plate.

FIGS. 11 and 12 are cross-sectional views similar to FIG. 10 showing alternative embodiments of the appliance.

FIG. 13 is a view, similar to FIG. 9, showing palatal placement of the device in a child's mouth.

FIGS. 14-16 are alternative embodiments of the appliance having protuberances of varying shapes.

DETAILED DESCRIPTION OF A PREFERRED EMBODIMENT

Figure 15:
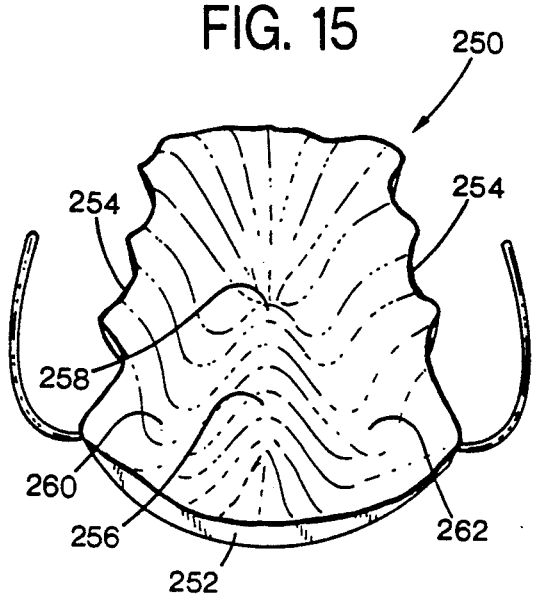

Several embodiments of an appliance are shown in the drawing for facilitating production of r sounds in a human subject. The appliance is particularly suited for producing a vowelized r that is generally denoted by the symbol ɝ. Once ɝ is taught using the device, the sound can be generalized by instruction to the consonant r.

FIGS. 1, 8 and 9 show an adult oral cavity or mouth 12 in which different embodiments of the appliance can be placed. Each mouth 12 has an upper dental arch and a lower dental arch. Only the right side of each dental arch is shown in FIG. 1, while the entire upper and lower dental arch is shown in FIG. 8 and the upper dental arch is shown in FIG. 9. The upper dental arch has adjacent central incisors 14, 15 on opposing right and left sides of the upper dental arch (FIGS. 8 and 9). The upper dental arch also includes opposing lateral incisors 16, 17, canine teeth 18, 19, premolars 20, 21 and 22, 23, first molars 24, 25, second molars 26, 27 and third molars 28, 29. The lower dental arch has corresponding teeth that are designated 14a-29a. The occlusal plane is an imaginary plane that passes through the surfaces at which the upper and lower teeth contact each other when the jaws are closed. The palatal vault is that area between the occlusal plane and the oral cavity roof 30 formed by the hard palate.

A first embodiment of the appliance 10 is shown in FIGS. 1-2 to include an acrylic head 36 molded around the tip of an insertion rod 38. Although the disclosed embodiment has an acrylic head, any non-toxic moldable material is suitable, such as thermoplastic resin or putty. Head 36 is a solid block having an arched top surface 40, an inferior surface 42, and opposing front and rear walls 44, 46. Arched top surface 40 substantially conforms to the palatal vault of a patient so that the appliance can rest comfortably against the roof of the mouth during use. The inferior surface 42 of head 36 is a flat surface that is preferably positioned coincident with the occlusal plane of the maxillary teeth in use. Front and rear surfaces 44, 46 (FIG. 1) are flat and parallel to one another, and perpendicular to inferior surface 42. A distal end of rod 38 is embedded in acrylic head 36, and the overall length of the rod is sufficient to protrude out of a subject's mouth (as shown in FIG. 1) when the appliance 10 is in a position described below that facilitates production of r sounds.

When using the embodiment of FIGS. 1-2, the appliance is inserted into the oral cavity between the dental arches by grasping the free proximal end of rod 38 and inserting the head of appliance 10 into the subject's open mouth. The appliance head 36 is positioned adjacent the posterior edge 31 of the hard palate. The arched top 40 is placed against the curve of the palatal vault, with the appliance head 36 extending transversely across the hard palate between the last erupted posterior maxillary teeth, for example the third molars 28, 29 on both sides of the upper dental arch. In an adult who lacks third molars, the head could be positioned between second molars 26, 27. In a child who lacks second and third molars, the head could be positioned between the first molars 24, 25. The anterior/posterior dimension of head 36 allows the head to be positioned transversely entirely between the last erupted molars (e.g. 28, 29) while the superior/inferior dimension is sufficient to allow arched top 40 to rest against the hard palate with flat inferior surface 42 at the level of the occlusal plane.

A second embodiment 50 of the appliance is shown in FIG. 3, having a head 52 with an arched top surface 54, a flat inferior surface 56 and front and rear surfaces 58, 60 (see FIGS. 3 and 4). The rod 38 of the prior embodiment is replaced with a handle 64. Along most of the length of handle 64, the handle is flat and presents a bottom surface that is substantially co-planar with the inferior surface 56 of appliance head 52. Acrylic head 52 is molded around the distal end of handle 64. A distal portion 66 of handle 64 adjacent head 52 is shaped like a truncated spoon that arches from the plane of handle 64 to the superior arcuate surface 54 of the head. This arched distal shape helps keep the handle away from the subject's tongue because the arched handle portion 66 conforms to the roof of the mouth. This arrangement diminishes the likelihood that appliance 50 will interfere with production of non-r sounds in the subject.

The size and shape of the palatal vault varies among different subjects. The size and shape of the appliance head 36 or 52 can preferably be modified (as shown in FIGS. 6 and 7) to change the dimensions of the head and better adapt it for unique use in individual patients. As shown in FIG. 6, the lateral and inferior dimensions of head 36 can be changed by applying pieces of putty or other malleable material 70, 72 to the lateral-inferior portions of the head. Alternatively, the superior-inferior dimension alone can be changed by adding putty to the inferior surface 42 of the head. Although not illustrated, any dimensions of the head can be altered by adding putty or taking it away. The anterior face, for example, can be augmented in this manner. These modifications can adapt the device to patients having palatal vaults with varying heights, widths and shapes.

In addition to customizing the shape of the head with putty, the heads can be manufactured in preselected sizes having dimensions that are more suitable for mouths of different sizes. The following table sets forth the preferred dimensions of several embodiments of the instrument:

TABLE I

| Dimension | Distance |
|---|---|
| Anterior-Posterior Extent of Block | 0.5-4 cm, preferably 0.5-2 cm, most preferably 0.5-1 cm |
| Inferior-Superior Extent of Block | 1-1.5 cm (preferably to occlusal plane) |
| Lateral Troughs | From midline to within 3 mm of lingual surface of |

TABLE I-continued

| Dimension | Distance |
|---|---|
| Insertion Rod | posterior teeth 10–14 cm |

The superior surface of the appliance fits or may preferably be fit to any lateral-central-lateral arc of the posterior hard palate to within 3–7 mm of the lingual surface of the posterior teeth.

Another embodiment of the appliance is shown in FIGS. 8–13. This embodiment of the device is a removable acrylic plate that resembles an orthodontic retainer that is clipped in the mouth of the patient using dental clasps. As best seen in FIG. 8, the appliance 80 is a dental plate 82 having an arched anterior plate portion that substantially conforms to the shape of the vault of the hard palate. A posterior portion of the plate 82 forms a block 84 that is positioned between the most posterior erupted maxillary molars, such as third molars 28, 29. Steel wires 86, 88 extend transversely from plate 82 between adjacent teeth and terminate in ball clasps 86a, 88a that fit respectively between maxillary molars 24, 26 and 26, 28 to retain appliance 80 in place. A similar pair of clasp wires 90, 92 project from plate 82 and extend between teeth 25, 27 and 27, 29, respectively. Each of clasps 90, 92 similarly terminates in a small ball 90a, 92a that helps the clasp retain appliance 80 in position. Other retention means can also be used.

A cross-section of block 84 is shown in FIG. 10, and includes an inferior surface 100 that extends between the molars 28, 29 from the level of the occlusal plane to the roof of the mouth when appliance 80 is in place, as shown in FIGS. 8 and 9. The anterior-posterior dimension of block 84 in this embodiment is no greater than the anterior-posterior dimension of molars 28. The lateral faces 102, 104 of block 84 are curved in the superior-inferior direction to form lateral gutters between the block 84 and upper dental arch. The anterior surface 106 of block 84 is gently inclined to present a slight slope from the occlusal plane to the palate, while the posterior surface 108 is more flat and more closely approximates a coronal plane.

Another embodiment of the appliance is shown in FIG. 11 wherein block 84 has been replaced by a rounded protuberance 112 that resembles an uvula and projects a sufficient distance from plate 82 to extend to the occlusal plane when the plate is in place in a subject's mouth. FIG. 12 shows yet another embodiment of the appliance wherein block 84 is replaced with a broad based arch 114. FIG. 13 shows an embodiment similar to FIGS. 8 and 9, but it is placed against the palate of a child who lacks second and third molars. Hence the block is positioned entirely between first molars 26,27

It has been found desireable to reduce the anterior-posterior dimension of the block as much as possible to avoid interfering with tongue movements during articulation. One approach to manufacturing the appliance is to fit the patient with a device such as that shown in FIGS. 8 and 9, then sequentially shave 1 mm off the posterior or anterior face of the block. After each 1 mm portion is taken off the appliance, the appliance is reinserted in the patient's mouth to determine whether ʒ can still be produced. If the patient can no longer say ʒ, the 1 mm segment is added back to the appliance.

The anterior-posterior dimension of the appliance is not restricted to the lingual dimension of the last erupted molars, although such a dimensional restriction has been found desireable because it minimizes interference with tongue movements. Some embodiments of block 84 can have an anterior-posterior dimension that extends along the lingual surfaces of two or more molars. The transverse distance of the block can also vary, for example from an uvula-like protuberance as in FIG. 11, to 10, to a block that extends completely transversely across the hard palate and touches the lingual surfaces of opposing molars on opposite sides of the upper dental arch.

Figure 16:
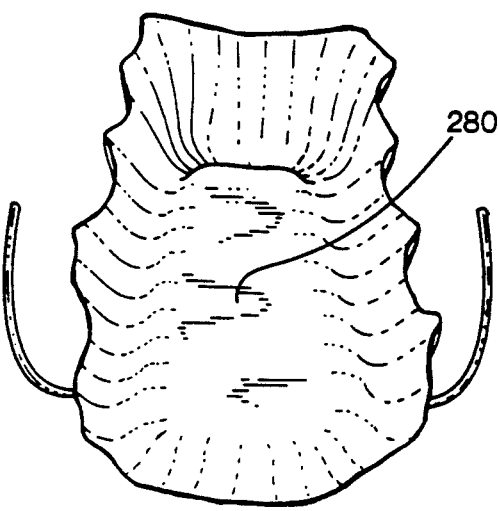

FIGS. 14–16 show several additional embodiments of the appliance drawn substantially to scale and shaded to illustrate their shape. In FIG. 14, plate 200 has a posterior edge 202 from which retention wires 204, 206 emerge. Wires 204, 206 curve anteriorly to retain plate 200 against the hard palate in a manner known in the art. A protuberance 208, having an uvula-shaped cross-section, extends from the plate a distance sufficient to reach the occlusal plane of a patient in whom the plate is placed, for example a distance of 1–1.5 cm. The greatest transverse width of the protuberance 208 is about 3 cm adjacent posterior edge 202, but the protuberance tapers in the anterior direction to a point 210. The lateral gutters 212, 214 widen from a width of about 2 cm adjacent posterior edge 202 to a distance of almost 3 cm at tip 210. The superior-inferior dimension of protuberance 208 similarly tapers in the anterior direction (toward tip 210) such that the tip 210 terminates above the occlusal plane when the appliance is in use. The superior-inferior dimension, for example, can taper from about 2 cm at edge 202 to about 1.5 cm at point 210. This reduction of the superior-inferior dimension has been found to reduce interference with tongue sounds that are required to produce non-r sounds. The anterior-posterior dimension of the protuberance of this particular embodiment is about 2 cm.

FIG. 15 shows another appliance 250 having a rear edge 252 and lateral indentations 254 that conform to the lingual surfaces of a patient's teeth. The protuberance 256 in this embodiment extends farther forward than in FIG. 14, having an anterior-posterior dimension of about 3.5 cm, and terminating in a rounded tip 258. The superior-inferior dimension of the appliance (from the roof of the mouth downward) tapers in the anterior direction (toward tip 258) such that the lateral gutters 260, 262 widen slightly in the anterior direction.

FIG. 16 is yet another embodiment in which the block has a substantially uniform superior-inferior dimension. The protuberance 280 is substantially rectangular in shape, and extends anteriorly more than half of the distance from the posterior edge of the hard palate to the central incisors. The anterior-posterior dimension in this embodiment is about 4 cm.

CASE HISTORIES

Fifty school age patients were studied who met the following criteria: (a) speech remediation for a minimum of six months in which the phoneme /r/ was targeted but in which no significant gain was made; (b) chronological age 8 to 12 years; (c) hearing within the normal range (d) normal intelligence; (e) normal language; (f) a residual /r/ articulation error with no known neurological deficits; (g) native American English speakers with English spoken in the home; (h) no orthodontic appliances that would interfere with the R-appliance. Three subjects were eliminated from the study because they failed to pass an auditory discrimination test.

Three expressive screening measures were then administered. These included the sounds-in-words subtest of the *Goldman Fristoe Test of Articulation* (Goldman & Fristoe, 1969) in which all words with the /r/ phoneme were scored; the *McDonald Deep Test of Articulation* (McDonald, 1964) for the /r/ phoneme; and a three-minute speech sample in response to a poster specific for the /r/ phoneme (Red Crater Grocery Store, 1970). Less than 25 percent correct productions of the consonant and/or vocalic /r/ items on the combination of all three tests was considered necessary for participation. Thirty-six children from the initial pool of 50 referrals met the criteria for participation in the study. The scores for the combined three screening measures ranged from 0 to 19 percent correct.

The 36 subjects were randomly assigned to one of four management groups with nine in each group. Group A: R-appliance and No Auditory Model; Group B: R-appliance and Auditory Model; Group C: No Auditory Model and no appliance; and Group D: Auditory Model and no appliance. There were no significant differences between the groups for any one of the three screening measures, as evidenced from t-tests on the highest group mean score versus the lowest group mean score ($p > 0.05$).

The R-appliance used was a removable acrylic palate with an acrylic block placed in the posterior portion as shown in FIG. 13. The anterior-posterior portion of the block extended from the mesial of the first molar to the distal of the first molar. The vertical dimension extended from the palate to the occlusal plane of the first molar. The transverse face of the block measured 20 mm on the posterior and tapered to 15 mm on the anterior aspect with a 3 mm gutter laterally from the occlusal plane on either side of the acrylic block. There was a slight slope on the anterior face of the block from the occlusal plane to the palate. The appliance was maintained in the arch by four metal wires with ball clasps on either side of the first molar (See FIG. 13).

All subjects were administered baseline measures prior to initiation of the study. These included ten trials for the /r/ sound in isolation, a 60-word pretest in which the /r/ occurred equally (10 times each) in different positions of words (initial, medial, final, blends, stressed and unstressed positions), and a three-minute spontaneous speech sample. The word level was selected as the final treatment step because the appliance is beneficial only up to the word level.

Following six weeks of intervention, the subjects in the appliance groups (A and B) showed a marked increase in their ability to correctly produce the target sound in isolation. The findings from the analysis of covariance show the main effect for appliance/no-appliance to be significant, $F(1,31) = 20.22$, $p\ 0.001$. The main effect for method of therapy (Auditory Model/No Auditory Model) was not significant, $F(1,31) = 0.00$, $p\ 0.05$. There was no interaction found between appliance level and therapy level, $F(1,31) = 2.78$, $p > 0.05$.

Figure 17:
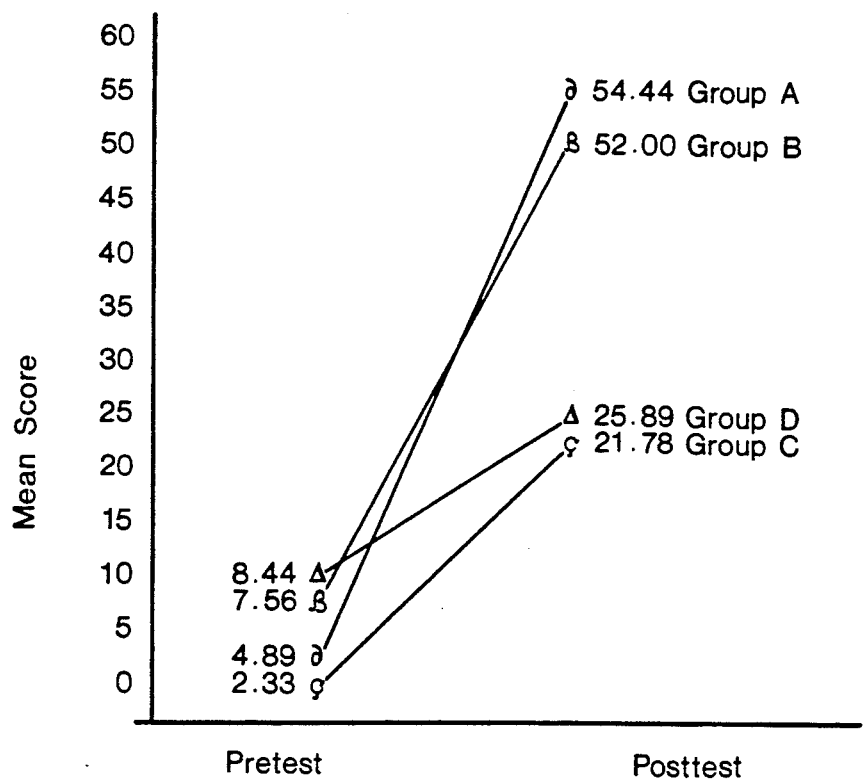
FIG. 17 is a graph showing pretest and posttest results that compares improvement producing r sounds with and without the appliance of the present invention.

The adjusted scores were used to compute confidence intervals. Confidence intervals set around the difference in group means demonstrated a significant difference in means between the appliance and non-appliance groups and this difference was in favor of Groups A and B, the appliance therapy groups. At the word level, the results following six weeks of intervention show that the mean scores for the appliance therapy groups (Groups A and B) for the production of the 60 pretest words were higher than those of the non-appliance groups. FIG. 17 shows a comparison of the pretest scores with the posttest scores.

The adjusted scores at the word level were used to compute confidence intervals. Confidence intervals set around the difference in group means for Groups A and D ($29.21 \pm 8.17$), Groups A and C ($32.18 \pm 8.04$), as well as Groups B and C ($29.24 \pm 8.52$) and Groups B and D ($26.27 \pm 7.89$). Results showed that use of the R-appliance with either therapy (Auditory Model or the No Auditory Model) is superior to the performance of non-appliance groups in facilitating the production of /r/ at the word level. The second confidence interval ($2.94 \pm 8.05$) was computed by finding the difference in group means between the two appliance groups, Group A and Group B. Based on these findings, there is no significant difference at the word level between the use of the R-appliance with the Auditory Model or No Auditory Model therapy.

To provide a more detailed analysis of pre-to posttest changes at the word level, a comparison of the production of the 60 /r/ pretest words was completed with the Oppenheim (1966) test for differences between proportions. A review of the appliance groups, Groups A and B, and non-appliance groups, Groups C and D, showed the appliance groups to have higher scores proportionately in each category (e.g., initial, medial, final, blends, stressed, unstressed). The difference in proportions was significant at $p < 0.05$ for each of the six categories (see Table 3).

The hallmark of a successful remediation program is generalization of the targeted structure during the course of intervention. Therefore, a measure of correct production for /r/ in spontaneous speech (a three-minute sample) was made prior to and at the end of the study. At the pretest, 10 of the subjects across the four groups made no correct productions of the target sound in their spontaneous speech. The other 26 subjects correctly produced /r/ from 3 percent to 17 percent of the time in a three-minute conversational speech sample. The findings from the analysis of covariance with /r/ in spontaneous speech show that the main effect for appliance (appliance/no appliance) was significant, $F(1, 34) = 64.16, p < 0.001$. The main effect for therapy (Auditory Model / No Auditory Model) was also significant, $F(1,34) = 11.52$, $p < 0.01$. In addition, there was a significant interaction between appliance use and therapy, $F(1, 34) = 5.34$, $p < 0.05$.

This example demonstrates that: (a) at all levels the appliance groups were significantly better than the non-appliance groups; (b) the difference between the two therapies (Auditory Model and No Auditory Model) without appliance use was not significant; and (c) at the word level and spontaneous speech levels, the Auditory Model therapy combined with the appliance was significantly better than No Auditory Model therapy combined with the appliance therapy. The Speech-language pathologists who participated in this study stated that, the R-appliance is a useful and effective tool in remediating residual /r/ errors.

EXAMPLE II

A twenty-two year old female with no preexisting defect in articulation experienced traumatic bilateral loss of hypoglossal innervation. Following the loss of innervation she was unable to pronounce r sounds. She was fitted with an appliance similar to that shown in FIGS. 14–15. Immediately after placement of the device in the patient's mouth, she was able to articulate both vocalic and consonant r sounds that she had been unable to articulate since her accident.

Having illustrated and described the principles of the invention in several preferred embodiments, it should be apparent to those skilled in the art that the invention can be modified in arrangement and detail without departing from such principles. We claim all modifications coming within the spirit and scope of the following claims.

I claim:

1. A method for facilitating production of r sounds in a human having a mouth with a palatal vault, a hard palate, and an occlusal plane, comprising:

selecting a person who has difficulty pronouncing r sounds;

placing in the mouth of the person who has difficulty pronouncing r sounds an appliance that fits adjacent a posterior edge of the hard palate and comprises a projection that extends across the palatal vault and projects inferiorly from the hard palate toward the occlusal plane a sufficient distance to improve an ability of the person to pronounce an r sound.

2. The method of claim 1 wherein the placing step comprises placing the appliance adjacent the edge such that the projection extends at least between opposing last erupted posterior maxillary teeth.

3. The method of claim 2 wherein the step of placing the appliance in the mouth comprises providing a projection on the appliance that extends downwardly substantially to the occlusal plane.

4. The method of claim 3 wherein the step of placing the appliance in the mouth comprises placing in the mouth a palatal plate that clips to a maxillary tooth and carries a block that extends below the plate between opposing molars.

5. The method of claim 1 wherein the placing step comprises placing the appliance against the hard palate.

6. The method of claim 5 wherein the step of placing the appliance in the mouth comprises placing the appliance against the hard palate with the appliance extending to the occlusal plane.

7. The method of claim 6 wherein the step of placing the appliance in the mouth comprises placing the appliance against the hard palate with the projection extending transversely across the palatal vault between opposing most posterior maxillary teeth.

8. The method of claim 7 wherein the placing step comprises placing the appliance inside a dental arch but not touching any maxillary teeth.

9. The method of claim 1 wherein the placing step comprises inserting into the mouth the appliance connected to an insertion handle, and positioning the appliance between maxillary teeth using the handle.

10. The method of claim 9 further comprising the step of providing the insertion handle with a curved distal portion that conforms to a shape of the hard palate anterior to the appliance, and the step of placing the appliance in the mouth comprises inserting into the mouth of the human the appliance connected to the insertion handle.

11. The method of claim 1 further comprising the step of modifying the appliance by adding a moldable material to the appliance to customize the appliance to produce r sounds in patients having palatal vaults of varying sizes and shapes.

12. The method of claim 1 further comprising the step of providing the appliance with a superior-inferior dimension that tapers in an anterior direction when the appliance is placed against the hard palate.

13. The method of claim 1 further comprising the step of providing the appliance with a transverse dimension that tapers in an anterior direction when the appliance is placed against the hard palate.

14. The method of claim 1 further comprising the step of providing the appliance with a projection with a transverse dimension that tapers in an anterior direction, and a superior-inferior dimension that tapers in the anterior direction, when the appliance is placed against the hard palate.

15. A method for facilitating production of r sounds in a human having a mouth with a palatal vault, a hard palate, and an occlusal plane, comprising the steps of:

selecting a person who has difficulty pronouncing r sounds;

providing an appliance that extends in an anterior-posterior direction no further than a mesial to a distal of opposing most posterior molars of the person, and in a superior-inferior dimension from the hard palate to the occlusal plane; and placing the appliance in the mouth of the person who has difficulty pronouncing r sounds, with the appliance adjacent a posterior edge of the hard palate and extending in an anterior-posterior direction from the mesial to the distal of the opposing most posterior molars, and in the superior-inferior dimension from the palate to the occlusal plane.

16. A method of facilitating production of r sounds in a person who has difficulty pronouncing r sounds, comprising the steps of:

selecting a person who has difficulty pronouncing r sounds; and inserting into a mouth of the person an appliance that fits against a hard palate between a most posterior pair of erupted molars, and from which a solid block with a flat bottom surface extends downwardly toward an occlusal plane a sufficient distance to improve an ability of the person to pronounce an r sound.

17. A method of facilitating pronunciation of r sounds in a person who has difficulty pronouncing r sounds, comprising the steps of:

selecting a person who has difficulty pronouncing r sounds;

placing in a mouth of the person a block that extends only between a most posterior pair of molars, and extends downwardly to an occlusal plane; and determining if the person is better able to articulate an r sound with the block in place.

18. A method of facilitating production of r sounds in a person who has difficulty pronouncing r sounds, comprising the steps of:

selecting a person who has difficulty pronouncing r sounds; and placing in a mouth of the person a dental plate that has an anterior portion adjacent front teeth and a posterior portion adjacent posterior teeth, wherein the anterior portion of the dental plate conforms to a shape of an anterior portion of a hard palate without interfering with tongue movements during articulation, and the posterior portion of the dental plate conforms to a shape of a posterior portion of the hard palate, with a protuberance extending downwardly from the posterior portion of the dental plate toward an occlusal plane to lower a height of the palatal vault below the protuberance.

19. The method of claim 18 further comprising the step or providing the protuberance with an uvula-shape that extends to the occlusal plane when the plate is in the mouth of the person.

20. The method of claim 18 further comprising the step of providing the protuberance with spaced anterior and posterior surfaces, such that the protuberance occupies a volume between the hard palate and occlusal plane from the posterior edge of the hard palate anterior a distance at least equal to a lingual dimension of a posterior pair of opposing molars in the person.

21. A method of facilitating production of r sounds in a person who has difficulty pronouncing r sounds, comprising the steps of:
selecting a person who has difficulty pronouncing r sounds, wherein the person has a mouth with a palatal vault and an occlusal plane; and
placing in the mouth of the person an appliance that lowers a height of the palatal vault between a pair of opposing molars and improves an ability of the person to pronounce an r sound.

22. The method of claim 21 wherein the appliance is inserted into the mouth of the person and manipulated therein with a handle.

23. The method of claim 21 wherein the appliance is placed between a most posterior pair of opposing molars.

24. The method of claim 21 wherein the appliance is retained in the mouth with a clasp.

25. A method of facilitating production of r sounds in a person who has difficulty pronouncing r sounds, comprising the steps of:
selecting a person who has difficulty pronouncing r sounds, wherein the person has a mouth with a palatal vault and an occlusal plane; and
lowering a height of the palatal vault between two opposing molar teeth on opposite sides of a dental arch a sufficient distance to improve an ability of the person to pronounce an r sound.

26. The method of claim 25 wherein the step of lowering the height of the palatal vault comprises inserting into the mouth an appliance that occupies a volume between the hard palate and occlusal plane.

27. The method of claim 26 further comprising the step of providing the appliance with an anterior-posterior dimension of 0.5–4.0 cm, and an inferior-superior dimension of 1.0–1.5 cm.

* * * * *

UNITED STATES PATENT AND TRADEMARK OFFICE
CERTIFICATE OF CORRECTION

PATENT NO. : 5,257,930
DATED : November 2, 1993
INVENTOR(S) : Robert W. Blakeley It is certified that error appears in the above-identified patent and that said Letters Patent is hereby corrected as shown below:

Title page, under U.S. Patent Documents, "4,112596" should read --4,112,596--.

Column 1, line 51, "(1978)" should read --(1978).--.

Column 5, line 54, "26,27" should read --26, 27.--.

Column 6, line 7, "11, to 10," should read --11, to an intermediate block with lateral gutters as in FIGS. 8-10,--.

Signed and Sealed this

Twenty-third Day of August, 1994

Attest:

BRUCE LEHMAN

Attesting Officer

Commissioner of Patents and Trademarks